(12) United States Patent
Schiffrin et al.

(10) Patent No.: US 6,576,475 B1
(45) Date of Patent: Jun. 10, 2003

(54) ASSAY SYSTEM AND NOVEL LABELLED COMPOUNDS FOR USE THEREWITH

(75) Inventors: David Schiffrin, Liverpool (GB); Robert Wilson, Liverpool (GB)

(73) Assignee: University of Liverpool, Liverpool (GB)

( * ) Notice: Subject to any disclaimer, the term of this patent is extended or adjusted under 35 U.S.C. 154(b) by 0 days.

(21) Appl. No.: 09/155,508

(22) PCT Filed: Apr. 1, 1997

(86) PCT No.: PCT/GB97/00908

§ 371 (c)(1),
(2), (4) Date: Dec. 23, 1998

(87) PCT Pub. No.: WO97/36931

PCT Pub. Date: Oct. 9, 1997

(30) Foreign Application Priority Data

Apr. 1, 1996 (GB) ............................................. 9606850

(51) Int. Cl.[7] ............................................. G01N 33/533
(52) U.S. Cl. ........................ 436/172; 556/15; 556/16; 556/136; 556/138; 556/143; 585/25; 435/7.1; 435/6; 530/391.3
(58) Field of Search ........................... 556/15, 16, 136, 556/138, 143; 435/7.1, 7.9, 7.94, 6; 204/194, 403; 585/25; 528/395; 436/172; 530/391.3

(56) References Cited

U.S. PATENT DOCUMENTS

| | | | | | |
|---|---|---|---|---|---|
| 4,205,952 A | * | 6/1980 | Cais | ............................. | 23/230 |
| 4,496,722 A | * | 1/1985 | Gallop et al. | .................. | 544/69 |
| 4,851,598 A | * | 7/1989 | Rosenblum et al. | .......... | 585/25 |
| 5,391,272 A | * | 2/1995 | O'Daly et al. | ......... | 204/153.12 |

FOREIGN PATENT DOCUMENTS

| | | |
|---|---|---|
| DE | 27 24 486 | 12/1977 |
| EP | 0-420987 A1 * | 2/1990 ..................... 17/26 |
| WO | WO 93/21530 | 10/1993 |

OTHER PUBLICATIONS

Bulgakov et al Izv. Akad. Nauk, ser. Khim. 1995 (12) 2529–30.*
Sato et al Electochem. Soc. 1993, 93–11 (proc. of the 5th international symposium on redox mechanisms and interfacial properties of molecules of biological importance 1993 299–310).*
Beer et al Polyhedron 1996 15 (14) 2457–2461.*
Ruch et al J. of Immunological Methods 63 1983 347–357.*
Journal of the American Chemical Society; vol. 115, No. 16, Aug. 11, 1993, p. 7053–7060, XP002032724, Badia et al.; "Intramolecular Electron—Transfer Rates in Ferrocene—Derivatized Glucose Oxidase".
Journal of Electroanalytical Chemistry; 448 (1998) ; p. 125–130; Wilson et al.; "Electrochemically Oxidized Ferrocenes as Catalysts for the Chemiluminesence Oxidation of Luminol".
Bull. Chem. Soc. Jpn.; 68; p. 165–171; (1995); Suzawa et al.; "Synthesis of Electoractive Protein Hybrid, Fec–BSA–Dig, and Its Application to a Novel Homogeneous Electrochemical Immunoassay".
Chemical Abstracts, vol. 99, 1983, p. 6; 99: 186905w; Examples of the use of an organometallic complex as a label for therapeutic molecules; Brossier et al.

* cited by examiner

Primary Examiner—Christopher L. Chin
(74) Attorney, Agent, or Firm—Merchant & Gould P.C.

(57) ABSTRACT

A Bis (cyclopentadienyl) metal complex of a derivative thereof is used as a label in an assay utilizing electrichemiluminescence or fluorescence detection means. The Bis (cyclopentadienyl) metal complex may comprise ferrocene or a derivative thereof which gives rise to a ferricinium ion on electrochemical oxidation.

9 Claims, 8 Drawing Sheets

ASSAY SYSTEM AND NOVEL LABELLED COMPOUNDS FOR USE THEREWITH

FIELD OF THE INVENTION

The present invention relates to an assay system and novel compounds for use therewith.

More particularly, it relates to an assay system which utilises the detection of light to qualitively or quantitively determine the presence of an analyte in a sample.

BACKGROUND OF THE INVENTION

There is a continuous and expanding need for rapid, highly specific methods of detecting and quantifying chemical, biochemical, and biological substances. Of particular value are methods for measuring small quantities of pharmaceuticals, metabolites, microorganisms and other materials of diagnostic value. Examples of such materials include narcotics and poisons, drugs administered for therapeutic purposes, hormones, pathogenic microorganisms and viruses, antibodies, metabolites, enzymes and nucleic acids The presence of such materials can often be determined by utilising an assay system which exploits the high degree of specificity which characterizes many biochemical and biological systems. Frequently used assay systems are based on, for example, antigen-antibody reactions, nucleic acid hybridization techniques, and protein-ligand reactions. In these assay systems, the presence or absence of an analyte is determined using an observable "label"—which has been attached directly or indirectly to one of the members of a binding pair.

Labels that can be detected luminometrically due to chemiluminescence or fluorimetrically as a result of the excitation of a fluorophore are particularly useful because of the sensitivity. In chemiluminescence light is emitted by a luminescent compound as a result of a chemical reaction. In fluorometry a fluorophore is excited with light of an appropriate wavelength and light that it emits is detected.

Electrochemiluminescence (ECL) is a specialised form of chemiluminescence in which the chemiluminescent reaction is preceded by an electrochemical redox reaction. Electrochemifluorescence is where a fluorophore is formed as the product of a chemical reaction which is preceded by an electrochemical redox reaction.

The present invention is concerned with assays that utilize electrochemiluminescence and electrochemifluorescence. It is also concerned with the enhancement of enzymatic reactions.

Amongst the prior art, the best known assay system utilising electrochemiluminescence (ECL) is a detection system developed by Igen Inc in which proteins and haptens are tagged with ruthenium II tris-bipyridine chelates which emit light when oxidised electrochemically in the present of tripropylamine which is also oxidised electrochemically.

Whilst this assay system has many benefits when compared to radioimmunoassay (RIA) and enzyme-linked immunosorbent assays (ELISA) it suffers a number of disadvantages compared with the invention described herein.

For example, sensitive detection systems for light (photomultipler tubes) are less sensitive to electrochemiluminescence at 620 nm (Igen) than to light at 425 nm (luminol), and each photon of light in the Igen system requires reoxidation of the label, whereas in the system described herein more than one photon of light is generated when the label is oxidised once.

DESCRIPTION OF THE INVENTION

It is one object of the present invention to provide an assay system which improves upon the current state of the art.

According to one aspect of the present invention there is provided a Bis (cyclopentadienyl) metal complex or a derivative thereof, for use as a label in an assay utilising electrochemiluminescence of fluorescence detection means.

Preferably, the Bis (cyclopentadienyl) metal complex is ferrocene, or a derivative thereof which gives rise to a ferricinium ion on electrochemical oxidation.

However, the use of other Bis (cyclopentadienyl) metal complexes or derivatives thereof are envisaged, such as, for example those of osmium or ruthenium.

The derivatives will include compounds which have the component of a binding pair linked to one of the cyclopentadienyl rings of the ferrocene, osmoscene or rutenocene. These derivatives are commonly referred to as ferrocenes, osmoscenes or ruthenocenes.

Thus, for example, a hapten or antigenic determinant might be linked to one or both of the cyclopentadienyl rings by reacting the amino group of a peptide with, for example, a carboxylic acid derivative of the ferrocene in a reaction as exemplified below:

Depending on the component of the binding pair, a number of well known chemical reactions can be utilised to covalently bond the first component of a binding pair to one or both of the cyclopentadienyl rings of, for example, ferrocene.

According to a further aspect of the present invention there is provided a Bis (cyclopentadienyl) metal complex derivative of the formula I:

(I)

Of course, depending on the reacting groups, the link could be a bond directly linking $C_1$ to the cyclopentadienyl ring.

Where M is a metal selected from the group consisting of iron, osmium and ruthenium;

$L_1$ is a link, and $C_1$ is a first component of a binding pair.

Most preferably M is iron.

The link is most likely to be formed from reacting a carboxylic acid, aldehyde, thiol or hydroxy derivative of, for example, ferrocene with a reactant group from the first component of the binding pair.

For example, where ferrocene monocarboxylic acid is reacted with, for example, the amino group of an antigen, the link will be:

Of course, depending on the reacting groups, the link could be a bond directly linking $C_1$ to the cyclopentadienyl ring.

The link $L_1$ will usually be determined by the nature of $C_1$. If $C_1$ is, for example, a protein, such as an antibody, $L_1$ is most likely to be a peptide bond (based on a carboxylic acid derivative of ferrocene and hydroxysuccinimide ester chemistry) and would be represented thus:

and gives rise to a ferrocene labelled protein which schematically looks like this:

If $C_1$ was DNA then $L_1$ could be a peptide bond (once again using hydroxysuccinimide ester chemistry). If $C_1$ is not a protein or DNA, then the $L_1$ may be an appropriate link. For example, where $C_1$ is the herbicide atrazine and the ferrocene is merceptomethylferrocene which has the structural formula:

The first component of the binding pair $C_1$ is preferably selected from:

i) Antibodies
ii) Antigens, and
iii) DNA

The derivative of formula I may include further modifications as shown in formula II where
M, $L_1$ and $C_1$ are as defined in formula I,
$L_2$ is a link, and
$F_1$ is a fluorophore.

Preferably, the fluorophore is fluorescein, or another fluorophore, which can act as an acceptor of energy from the chemiluminescence reaction by resonance energy transfer.

The aim of attaching fluorescent compounds to the ferrocene is to utilise the phenomenon known as resonance energy transfer in which energy is transferred over short (effectively less than 10 nanometers) distances from an excited molecule (in this instance the product of a chemiluminescent reaction) to an fluorescent acceptor molecule.

The compounds of formula I and II may be further modified by the inclusion of substituents on the cyclopentadienyl ring which do not affect the ability of the compounds to bind a second component of the binding pair but which modulate the electrochemistry of the ferrocene.

Additional groups could be used to module the electrochemistry (for example ferrocene acetic acid is oxidised at a lower redox potential than ferrocene monocarboxylic acid) and so modulating substituents may be used.

According to yet a further aspect of the present invention there is provided a method for determining the presence of an analyte in a sample which is one of first and second components of a binding pair, the method comprising:

initiating, at an electrode, a reaction between the reactants of a chemiluminescent or a fluorescent detection system with a Bis (cyclopentadienyl) metal complex or derivative thereof, e.g. a complex or derivative of the formula I or II, and identifying the presence of the analyte from a change in light emission due to the binding of the second component to the first component such that the Bis (cyclopentadienyl) metal complex or derivative thereof becomes electroinactive and is prevented from catalyzing the electrochemiluminescent or fluorescent reaction of the electrochemiluminescence or fluorescence detection system.

The invention derives from the observation that the chemiluminescent oxidation of luminol (3-aminophthalic acid) by hydrogen peroxide can be catalyzed/initiated by the electrochemical oxidation of ferrocene derivatives.

Figure 1:
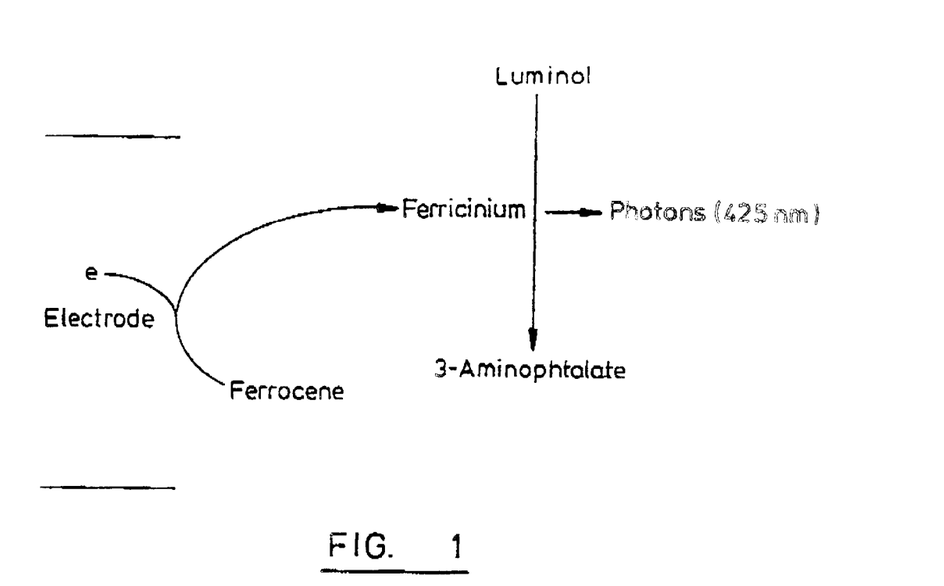
FIG. 1 shows how ferricinium ions catalyze chemiluminescence.

Without wishing to be bound by theory, it is believed that in the case of ferrocene and derivatives thereof ferricinium ions catalyze the chemiluminescence as shown in FIG. 1, which illustrates the proposed mechanism for the catalytic effect of ferricinium on the chemiluminescent reaction of luminol with hydrogen peroxide. It is believed that the corresponding Bis (cyclopentadienyl) metal complexes of the group VIII metals, Ruthenium and Osmium would behave in a similar manner.

This mechanism resembles the way that some proteins such as, for example, horseradish peroxidase, catalase, and microperoxidase catalyze the chemiluminescent reaction between luminol and hydrogen peroxide. These proteins contain Fe (III) which is thought to reach with hydrogen peroxide and form a complex that oxidizes luminol chemiluminesently.

These proteins also catalyze a wide range of other reactions that yield a variety of products including coloured dyes, electroactive compounds, fluorescent compounds and other luminescent compounds. For example, horseradish peroxidase catalyzes the oxidation of homovanillic acid to a fluorescent product. This reaction is also catalyzed by ferrocenes as shown in the following equation, Non-Fluorescent (Homovanillic acid) Fluorescent and it is likely that other reactions catalyzed by these proteins, many of them analytically useful, will also be catalyzed by ferrocenes.

This discovery opens the way for a number of improved assays and the production of novel labelled derivatives of Bis (pentadienyl) metal complexes.

For a homogenous immunoassay to be successful, there must by a way for distinguishing bound and unbound analyte. One way to do this is to modulate the signal from a label such as an enzyme, a fluorophore, or a redox compound, such as, for example, ferrocene so that the signal is proportional to the amount of analyte in the sample. An alternative way is to activate the label when it binds to the solid phase with radioisotopes, fluorescently or electrochemically.

In the present invention, it is shown with reference to ferrocene and its monocarboxylic acid derivative, that electrochemically oxidized ferrocenes catalyze the chemiluminescent oxidation of luminol and the oxidation of other compounds, by hydrogen peroxide.

The reaction was found to be similar to that of horseradish peroxidase, which is used as a label in immunoassays, except that chemiluminescence can be initiated at the surface of an electrode where ferricinium is generated electrochemically. This difference means that ferrocene labels could be used to detect material bound to the surface of an electrode.

This has been shown in the present invention by detecting a layer of labelled albumin adsorbed on an indium tin oxide-coated glass electrode as a model for a separation-free immunoassay. Ferrocenes oxidised at an indium tin oxide-coated glass electrode catalyze the chemiluminescent reaction of luminol with hydrogen peroxide and the chemifluorescent reaction of homovanillic acid with hydrogen peroxide. The catalytic reaction has been studied with ferrocene derivatives both in solution and when covalently attached to ovalbumin adsorbed on the electrode. Ferrocenes also enhance other analytically useful enzyme catalyzed reactions.

The invention will be described further, by way of example only, with reference to ferrocene.

EXPERIMENT 1

Investigation of electrochemiluminescence in solution
Linear Sweep Voltammetry Reactions were carried out in 0.1 M TRIS buffer, pH 8.0 that contained 0.1 M NaCl. Solutions of ferrocenemonocarboxylic acid, luminol and hydrogen peroxide were mixed before the experiments so that the final concentrations were 100 $\mu$M ferrocene, 100 $\mu$M luminol and 1 mM hydrogen peroxide. Light intensity was recorded as the potential was swept from 0 to 350 mV at 1 mV s$^{-1}$. In the control experiment, ferrocenemonocarboxylic acid was omitted from the solution.
Electrochemiluminescence Reaction at a Fixed Potential Reactions were carried out in the same solution described previously except that electrochemiluminescence was initiated by stepping the potential from 0 to 350 mV. Light and current were measured simultaneously. The effect of pH on the reaction was investigated by adjusting the pH of the solutions with hydrochloric acid. The influence of EDTA (10 mM) and p-indophenol (0.5 mM) on light intensity was also investigated.

RESULTS

Figure 2:
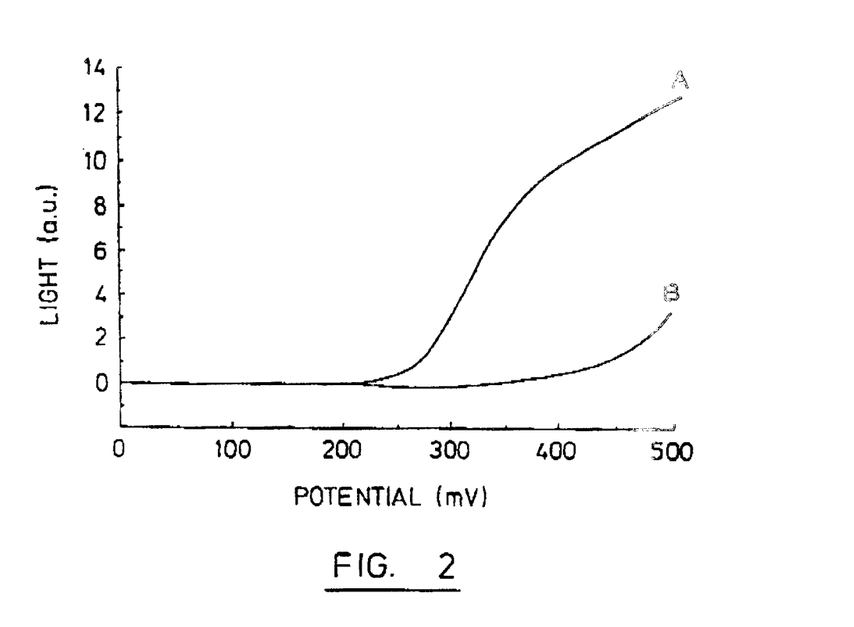
FIG. 2 shows the dependence of chemiluminescence on potential at pH 8.0 in 0.1 M TRIS buffer with 0.1 M NaCl, 1 mM hydrogen peroxide and 100 uM luminol.

FIG. 2 shows the dependence of chemiluminescence on potential at pH 8.0 in 0.1 M TRIS buffer with 0.1 M NaCl, 1 mM hydrogen peroxide and 100 $\mu$M luminol. Curve (A) shows the reaction catalyzed by 100 $\mu$m ferrocenemonocarboxylic acid, and curve (B) shows the uncatalyzed reaction. The sweep rate was 1 mV s$^{-1}$. When ferrocenemonocarboxylic acid was present, light emission was observed at potentials of about 200 mV more negative than when it was absent.

Figure 3A:
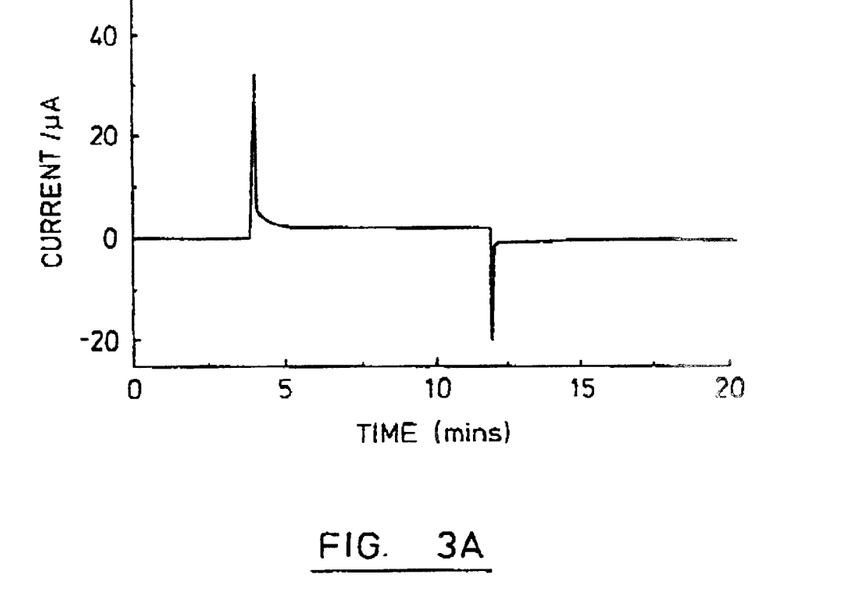
FIGS. 3(A)–3(B) shows the effect on current and light intensity of stepping the potential from 0 to 350 mV.
Figure 3B:
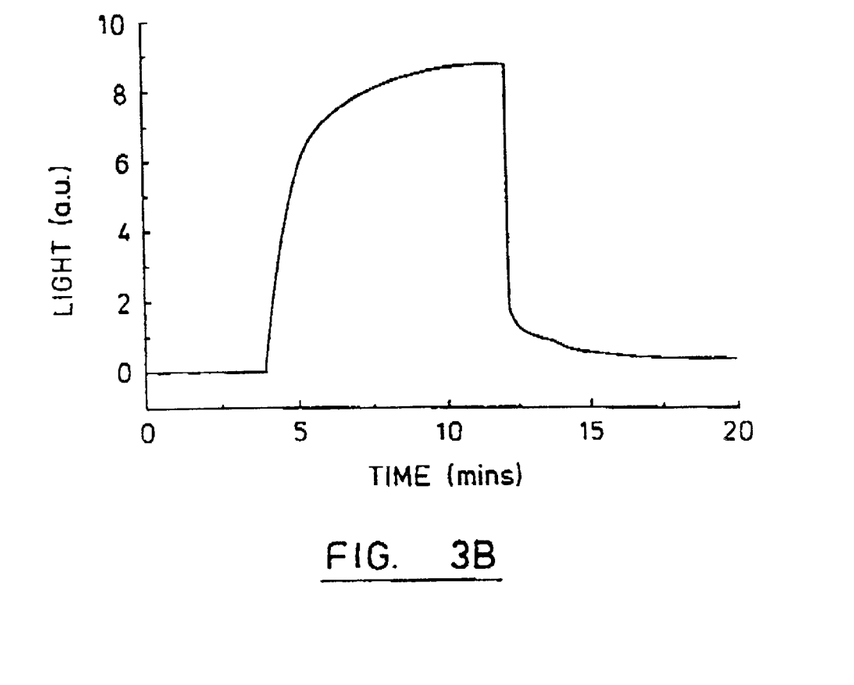

FIG. 3 shows the effect on current and light intensity of stepping the potential from 0 to 350 mV. Profile (A) shows the effect on current, and profile (B) shows the effect of light intensity transients for a potential step from 0 to 350 mV for 100 μm ferrocenemonocarboxylic acid at pH 8.0 in 0.1 M TRIS buffer with 0.1 M NaCl, 1 mM hydrogen peroxide and 100 μm luminol.

The current decayed as expected for a diffusionally controlled process, but light intensity continued to increases for a long period of time.

Figure 4:
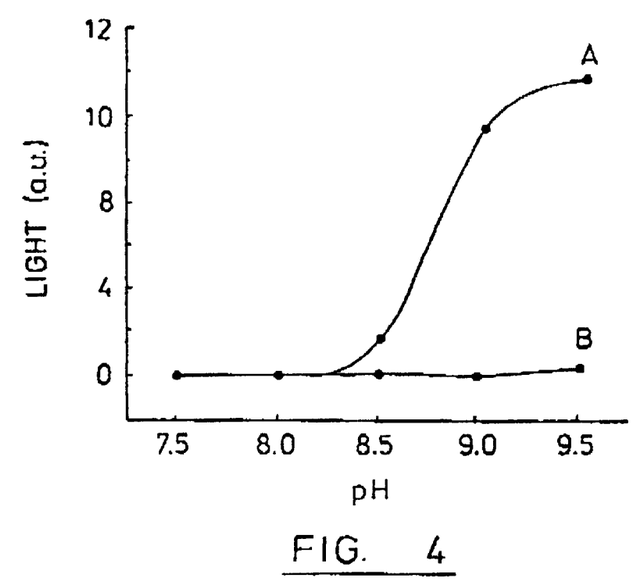
FIG. 4 shows the dependency of chemiluminescence on pH at 350 mV in 0.1 M TRIS buffer with 0.1 M NaCl, 1 mM hydrogen peroxide and 100 uM luminol.

The effect of pH on light emission is shown in FIG. 4 which shows the dependency of chemiluminescence on pH at 350 mV in 0.1 M TRIS buffer with 0.1 M NaCl, 1 mM hydrogen peroxide and 100 μM luminol. Curve (A) shows the reaction catalyzed by 100 μM ferrocenemonocarboxylic acid, and curve (B) shows the reaction uncatalyzed.

The increase in light intensity with pH is typical of luminol reactions.

When horseradish peroxidase is used to catalyze the chemiluminescent reaction between luminol and hydrogen peroxide, compounds such as p-indophenol greatly enhance the light intensity. However, this compound has no effect on the reaction catalyzed by ferrocenes. EDTA, which is capable of chelating the iron center in ferricinium, reduced the light intensity by 25%.

EXPERIMENT 2
Preparation of Ferrocene-Labelled Ovalbumin

Ovalbumin was dissolved in 0.1 M phosphate buffer, pH 7.5 that contained 0.1 M NaCl. The N-hydroxy-succinimide ester of ferroceneacetic acid (SFA) was prepared. It was dissolved in ethanol and added to the ovalbumin solution so that the final concentrations were 10% (v/v) ethanol, 10 mg mL$^{-1}$ ovalbumin, and 1 mM SFA. The solution was allowed to stand for 1 h at room temperature and then loaded onto a column packed with SEPHADEX G-15 (void volume 11 ml) and eluted with distilled water. The first 3 ml of elute after the void volume was retained. The concentration of protein in the retained elute was determined colorimetrically with coomassie blue. The concentration of iron was determined by flame atomic absorption spectroscopy after digesting the ovalbumin with nitric acid at 100° C. All experiments were repeated with an ovalbumin solution that had not been treated with SFA.

Cyclic Voltametry of Adsorbed Ovalbumin

ITO-coated glass electrodes were immersed for 10 min in the retained elute diluted 1:1 with 0.2 M citric acid then thoroughly washed with 0.1 M citric acid. The electrodes were cycled between 0 and 700 mV SCE at 10 and 100 mV s$^{-1}$ in 0.1 M citric acid. The area of the working electrode was 1 cm$^2$. Electrodes were also cycled in 0.1 M TRIS buffer, pH 9.0 that contained 0.1 M NaCl.

Electrochemiluminescence of Adsorbed Ovalbumin

The potential of electrodes with a layer of adsorbed ovalbumin was stepped from 0 to 350 mV in 0.1 M TRIS buffer, pH 9.0 that contained 0.1 M NaCl and the light intensity was recorded. A similar experiment was carried out with unlabeled ovalbumin.

RESULTS
Ferrocene-Labeled Ovalbumin.

The concentration of ovalbumin in the retained eluate from the SEPHADEX G-15 column was 8.6 mg ml$^{-1}$ for the ferrocene-labeled ovalbumin and 8.7 mg ml for the unlabeled ovalbumin solution. This suggests that the incorporation of ferroceneactic acid into the protein did not interfere with the method used for protein determination. Ovalbumin has a molecular mass of 44 000 Da, and therefore, the concentration in the eluate was 0.19 mM. Atomic absorbance spectroscopy indicated that the concentration of iron in the labeled ovalbumin solution was 26 ppm. Assuming all the additional iron was present as ferrocene, these results imply that there were two or three ferrocene molecules attached per molecule of ovalbumin.

Figure 5:
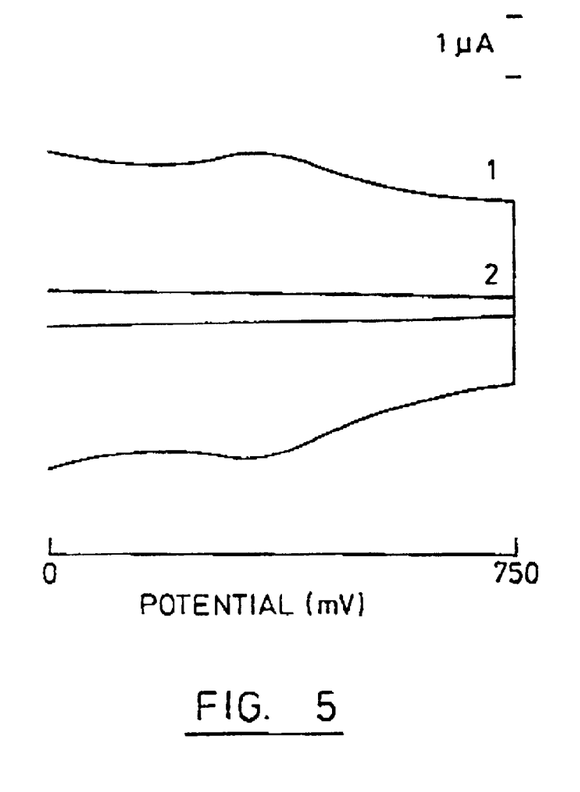
FIG. 5 shows a cyclic voltammogram of ferrocene-labeled ovalbumin adsorbed on an ITO electrode in 0.1 M citric acid.

Ferricinium ions are unstable in aqueous solution. This is particularly noticeable in cyclic volammetric experiments when they are present as a monolayer on the surface of an electrode. When ITO-coated electrodes were immersed in ferrocene-labeled ovalbumin in citric acid, a layer of labeled protein adsorbed into the electrode as shown by cyclic Voltammetry (FIG. 5). FIG. 5 shows cyclic voltammogram of ferrocene-labeled ovalbumin adsorbed on an ITO electrode in 0.1 M citric acid: (A) 100 mV S$^{-1}$, (B) 10 mV S$^{-1}$. Potentials vs SCE. Strong surface attachment was evidence because these peaks did not change when the electrode was washed with 0.1 M citric or distilled water; no peaks were observed for electrodes immersed in unlabeled ovalbumin. The average charge under the peaks (0.6 μC cm$^{-2}$) corresponded to about four ferrocene molecules/nm$^2$. Ovalbumin is a disk-shaped protein with a major and minor axis of 23 and 6.3 nm, respectively. If each molecule contained 2 equivalents of ferrocene and the electrode surface was perfectly smooth, an adsorbed monolayer should contain a maximum of 0.5 ferrocenes/nm$^2$. A value of 4 ferrocene molecules/nm suggests that there was more than one layer of protein adsorbed on the surface and/or that the electrode surface was not perfectly smooth. The surface of ITO is indeed very rough on an atomic scale as shown by scanning tunnelling and atomic force microscopies. Repeated cycling of the electrodes did not reduce the area under the ferrocene peaks, but when they were cycled in pH 9.0 TRIS buffer, the peaks rapidly decayed. This may be due to the decrease in stability of ferricinium ions in the absence of citric acid, which is known to stabilize it.

Electrochemiluminescence of Adsorbed Ferrocene Labeled Ovalbumin

ITO-coated electrodes with a layer of adsorbed ferrocene-labeled ovalbumin were washed with 0.1 M TRIS buffer, pH 9.0 that contained 0.1 M NaCl. These were then immersed in the same buffer that also contained 10 mM hydrogen peroxide and 100 μM luminol in the cell fluorometer electrochemical cell. The potential was stepped from 0 to 350 mV and the light intensity recorded. The procedure was repeated with electrodes treated with unlabeled ovalbumin and FIG. 6 compares light emission for labelled and unlabeled ovalbumin.

Figure 6A:
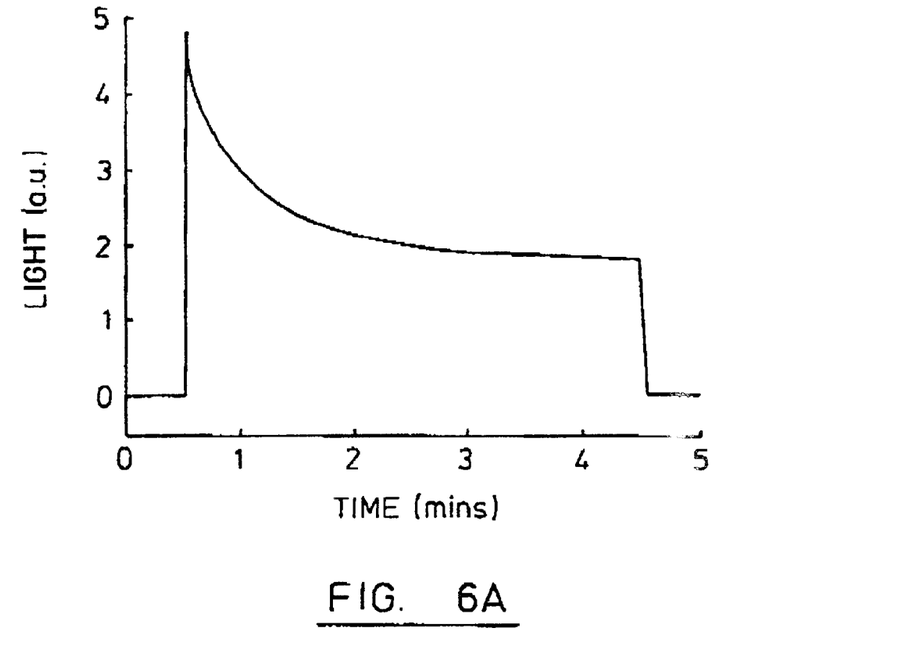
FIGS. 6(A)–6(B) show electrochemiluminescence of ITO electrodes with adsorbed ovalbumin.
Figure 6B:
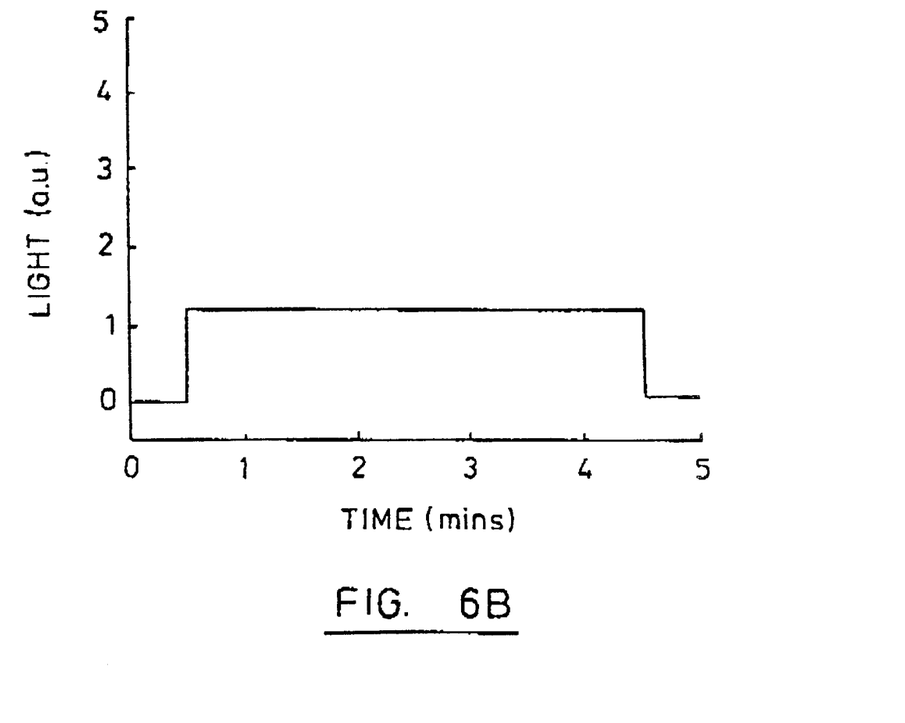

FIG. 6 shows electrochemiluminescence of ITO electrodes with adsorbed ovalbumin when the potential was stepped from 0 to 350 mV vs AgCl at pH 9.0 in 0.1 M TRIS buffer, with 0.1 M NaCl 1 mM hydrogen peroxide, and 100 μm luminol: (A) ferrocene-labeled ovalbumin (B) unlabeled ovalbumin.

This Electrochemiluminescence detection of ferrocene labeled ovalbumin adsorbed on an electrode suggests that it may be possible to detect ferrocene labeled antibodies in the same way. This could be used to determine the amount of analyte in solution in competitive immunoassays in which labeled antibodies partition between analyte in solution and analyte attached to an electrode.

For example, ferrocene attached to bovine serum albumin labeled with digoxin becomes electroinactive in the presence of antibodies to digoxin, and electrochemiluminescence detection may increase the sensitivity.

Ferrocenes could also be used instead of ruthenium tris (bipyridyl) labels in electrochemiluminescence immunoassays and DNA assays.

It may be possible to use ferrocene as an antigen label in homogenous immunoassays for small molecules, like drugs and pesticides. The ferrocene molecule is small and therefore it may becomes electroinactive when enveloped by the antibody or because the diffusion coefficient decreases when it is bound by the antibody, in the same way that daunomycin-labeled biotin becomes electroinactive in the present avidin.

The above proposals are supported by the results presented herein and are based on the premise that the ferricinium ions catalyze chemiluminescence as shown in FIG. 1.

If ferrocinium forms a complex between hydrogen peroxide and luminol, the effect of EDTA on the chemiluminescence reaction would be explained by its ability to compete with hydrogen peroxide for the iron centre in ferricinium. Like the heme proteins mentioned before, ferricinium has been shown to be a very efficient catalyst of luminol chemiluminescence and subnanomolar amounts could be readily detected. To account for the delay between the start of the electrochemical reaction and maximum chemiluminescence, it is proposed that ferricinium decays and light reaches a maximum when the rate at which ferricinium is generated electrochemically is equal to the rate at which it is destroyed. Ferricinium is unstable and decays to Fe (III), which also catalyzes the chemiluminescence reaction between luminol and hydrogen peroxide.

EXPERIMENT 3
Electrochemifluorescence Reaction at a Fixed Potential

Reactions were carried out under the same conditions used for electrochemiluminescence at a fixed potential except that luminol was replaced by 100 $\mu$M homovanillic acid, the potential was stepped from 0–300 mV instead of 0–350 mV, and a solution was excited with light of 315 nm. Once again ferrocene monocarboxylic acid was omitted from the control.

RESULTS
Electrochemifluorescence Reactions at a Fixed Potential

Figure 7:
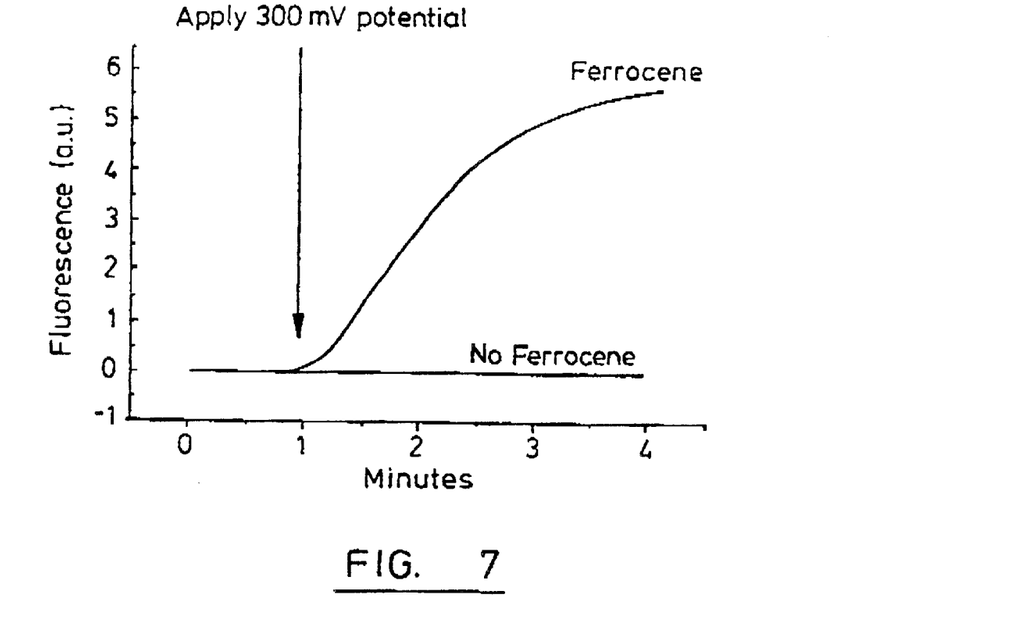
FIG. 7 illustrates the effect on fluorescence at 425 nm of stepping potential from 0 to 300 mV.

FIG. 7 illustrates the effect on fluorescence at 425 nm on stepping the potential from 0 to 300 mV. On restoring the potential to 0 mV the fluorescence intensity remains unchanged.

EXPERIMENT 4
Enhancement of enzymatic reactions

Horseradish peroxidase was added to a solution of luminol (5 mM) and hydrogen peroxide (10 mM) in 0.1 M TRIS buffer, pH 8.0, that contained 0.1 M NaCl and 250 $\mu$M ferocenemonocarboxylic acid, and the light intensity at 425 nm vs time was recorded. In a control experiment ferrocenemonocarboxylic acid was omitted.

RESULTS
Enhancement of enzymatic reactions

Figure 8:
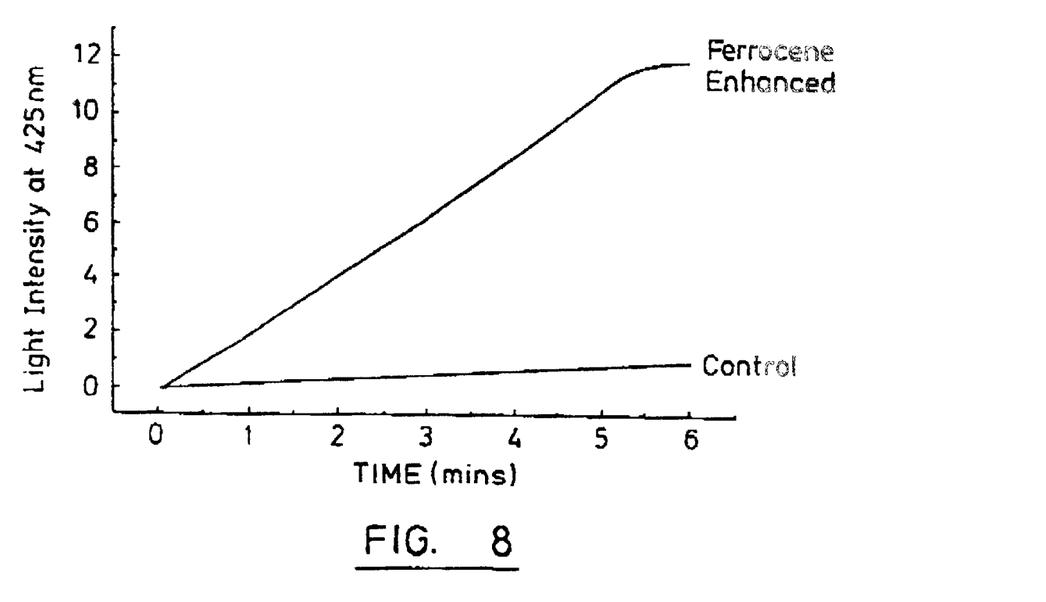
FIG. 8 shows the effect of ferrocenemonocarboxylic acid on light intensity.

The effect of ferrocenemonocarboxylic acid on light intensity is shown in FIG. 8. FIG. 8 shows the enhancement of chemiluminescence reaction catalyzed by peroxidase. Identical amounts of peroxidase were added to both solutions at zero time. Although luminol and ferrocenemonocarboxylic acid are both substrates for horseradish peroxidase the ferrocene is preferentially oxidized. Therefore the concentrations of ferricinum ions increases and this catalyzes the chemiluminescent reaction of luminol with hydrogen peroxide. From this, and other results presented previously, it is inferred that ferrocenes will also enhance many other enzyme catalyzed reactions, including enzyme catalyzed fluorescence reactions.

These results support a number of potential applications which are further illustrated and supported with reference to FIGS. 9 to 11 below.

Figure 9:
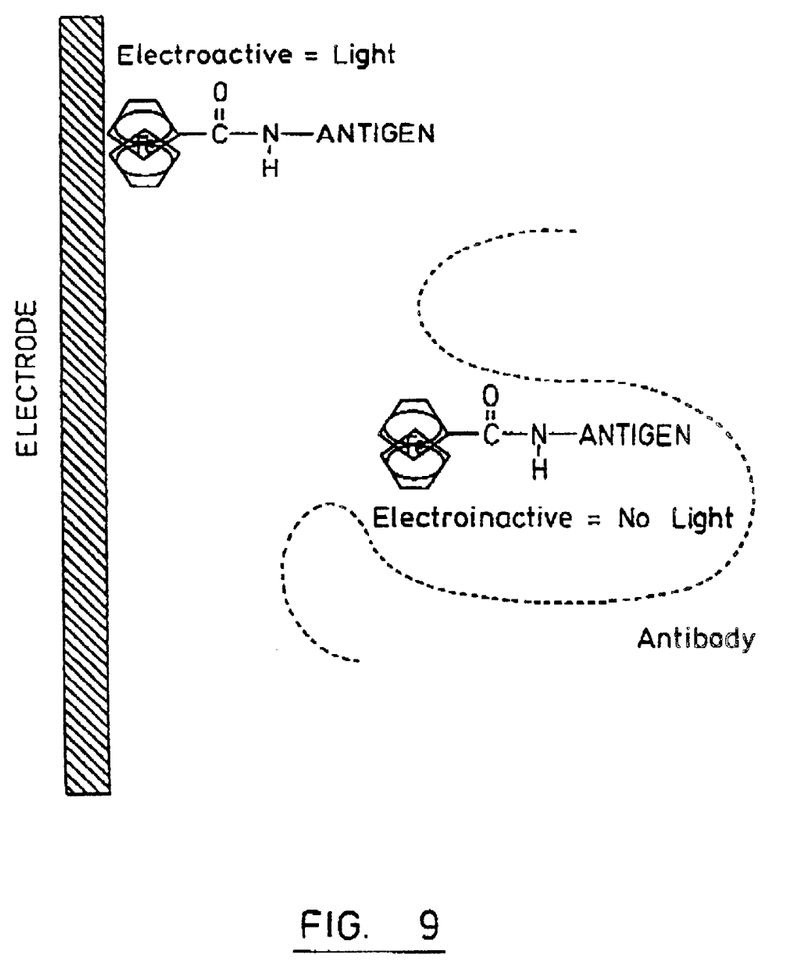
FIG. 9 illustrates the use of compounds of formula I and II as labels in competition immunoassays.

FIG. 9 illustrates the use of the compounds of formula I and II as labels in competition immunoassays. In the illustrated example, the ferrocene label is "switched off" when antibodies bind to the antigen by a combination of diffusion and screening effects. This explanation derives from a comparison with duanomycin labeled biotin which becomes comparison with duanomycin labeled biotin which becomes electroinactive in the presence of avidin. Examples of analytes that might be detected in this kind of immunoassay are drugs and hormones which are small molecules that need to be detected in the nanomolar and micromolar range.

Figure 10:
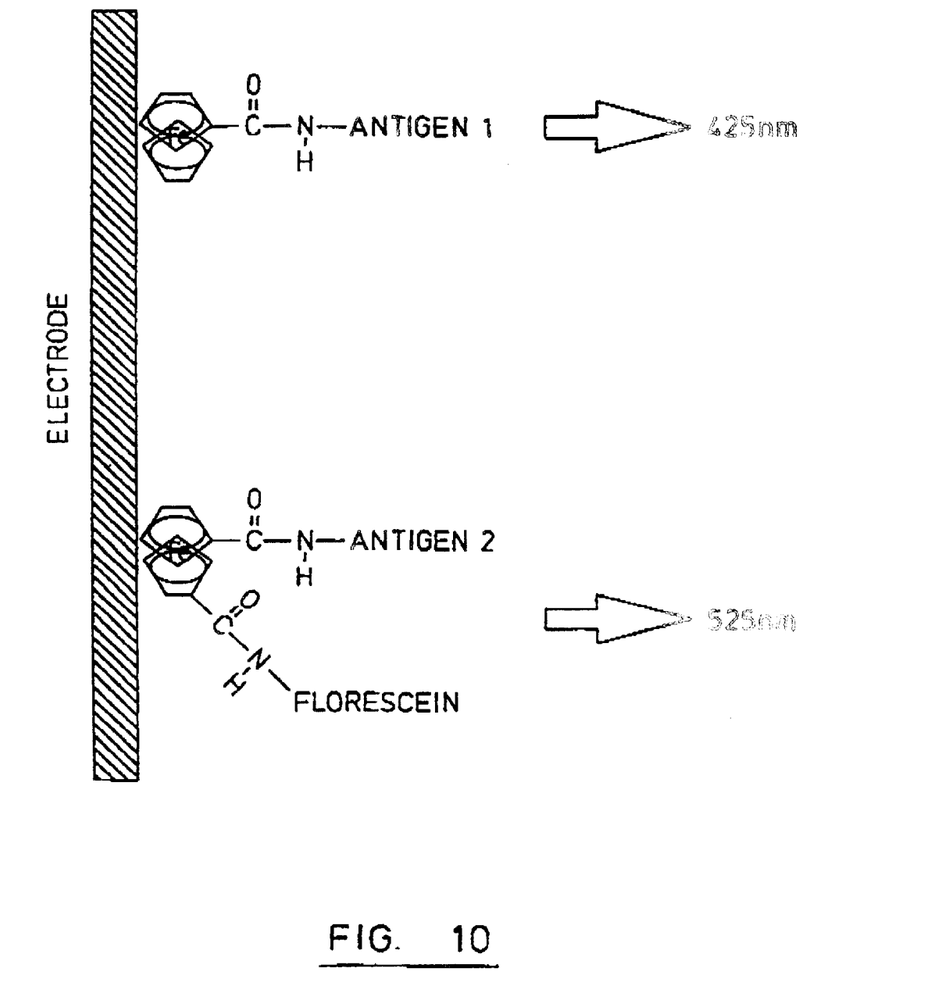
FIG. 10 illustrates a modification of the assay system illustrated in FIG. 9 where compounds of formula I and II are used as labels in a multianalyte immunoassay.

FIG. 10 illustrates a modification of the assay system illustrated in FIG. 9 where compounds of formula I and II are used as labels in a multianalyte immunoassay. As well as tagging one component of a binding pair to a cyclopentadienyl ring, a molecule such as fluorescein, which will accept energy from a chemiluminescent compound and emit it at another wavelength, is bound to the same or a different cyclopentadienyl ring. When located close to the ferrocene the fluorescein is able to couple the emitted light and emit it at a different wavelength.

Figure 11:
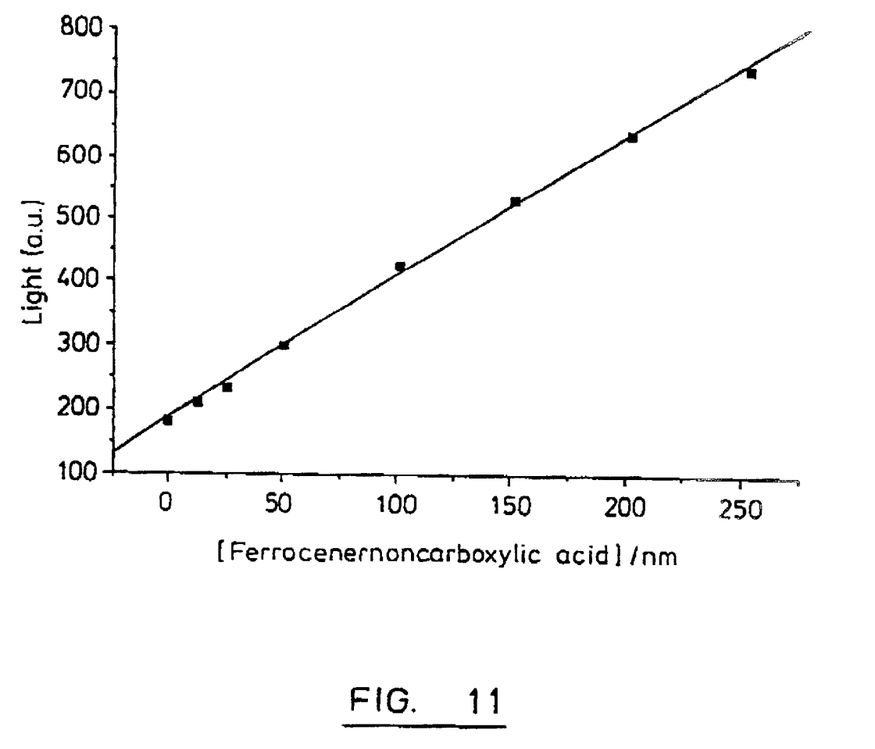
FIG. 11 shows the relationship between light transmitted and ferrocene monocarboxylic acid concentration.

FIG. 11 shows the relationship between light transmitted and ferrocene monocarboxylic acid concentration and illustrates the fact that the methods described could be made to detect analyte at nanomolar concentrations.

What is claimed is:

1. A bis-cyclopentadienyl derivative of formula II:

wherein:
M is a metal selected from the group consisting of iron, osmium and ruthenium;
$L_1$ is a linking moiety;
$L_2$ is a linking moiety;
$C_1$ is a first component to have a binding pair; and
F is a fluorophore.

2. A derivative according to claim 1, wherein M is iron.
3. A derivative according to claim 1, wherein the fluorophore is an acceptor of energy of chemiluminescence reaction by resonance energy transfer.
4. A derivative according to claim 1, wherein the fluorophore is fluorescein or a derivative thereof.
5. A derivative according to claim 1, wherein $C_1$ is a first component of a binding pair linked by a linking moiety to one or both of the cyclopentadienyl rings and is a protein, antibody, antigen or DNA.
6. A derivative according to claim 1, wherein $C_1$ is a protein or DNA and the linking moiety is a peptide.
7. A derivative according to claim 1, wherein $C_1$ is a first component of a binding pair linked by a linking moiety to one or both of the cyclopentadienyl rings and is a protein, antibody, antigen or DNA.
8. A derivative according to claim 1, wherein $C_1$ is a protein or DNA and the linking moiety is a peptide.
9. A derivative according to claim 1, wherein $L_1$ is
(a) formed from the reaction of a carboxylic acid, aldehyde, thiol or hydroxy group with a group of the first component of the binding pair, (b)

formed from the reaction of a ferrocene monocarboxylic acid with the amino group of an antigen, or (c) a bond directly linking the first component of a binding pair to a cyclopentadienyl ring.

* * * * *